United States Patent [19]
Sauer et al.

[11] Patent Number: 5,584,793
[45] Date of Patent: Dec. 17, 1996

[54] ENDOSCOPE ATTACHMENT FOR CHANGING ANGLE OF VIEW

[75] Inventors: Jude S. Sauer, Pittsford; Roger J. Greenwald, Holley; Michael G. Oravecz, Rochester; Alex Kobilansky, Pittsford, all of N.Y.

[73] Assignee: United States Surgical Corporation, Norwalk, Conn.

[21] Appl. No.: 488,268

[22] Filed: Jun. 7, 1995

Related U.S. Application Data

[62] Division of Ser. No. 134,536, Oct. 8, 1993.

[51] Int. Cl.⁶ .................................................. A61B 1/04
[52] U.S. Cl. ...................... 600/121; 600/175; 206/310
[58] Field of Search .............................. 206/363, 364, 206/438, 370; 600/102, 121, 124, 175, 129, 160

[56] References Cited

U.S. PATENT DOCUMENTS

| | | |
|---|---|---|
| 3,089,484 | 5/1963 | Hett . |
| 3,818,902 | 6/1974 | Konoshita et al. . |
| 4,113,354 | 9/1978 | Yamasita et al. . |
| 4,195,904 | 4/1980 | Yamashita . |
| 4,398,811 | 8/1983 | Nishioka et al. . |
| 4,500,181 | 2/1985 | Takahashi . |
| 4,615,333 | 10/1986 | Taguchi . |
| 4,640,577 | 3/1987 | Tsuno . |
| 4,646,722 | 3/1987 | Silverstein et al. . |
| 4,667,656 | 5/1987 | Yabe . |
| 4,671,630 | 6/1987 | Takahashi . |
| 4,684,224 | 8/1987 | Yamashita et al. . |
| 4,721,097 | 1/1988 | D'Amelio . |
| 4,727,859 | 3/1988 | Lia . |
| 4,730,909 | 3/1988 | Takahashi . |
| 4,741,326 | 5/1988 | Sidall et al. . |
| 4,746,203 | 5/1988 | Nishioka et al. . |
| 4,747,661 | 5/1988 | Ohkuwa . |
| 4,770,163 | 9/1988 | Ono et al. . |
| 4,784,118 | 11/1988 | Fantone et al. . |
| 4,787,370 | 11/1988 | Kanamori . |
| 4,815,833 | 3/1989 | Zobel et al. . |
| 4,819,620 | 4/1989 | Okutsu . |
| 4,838,246 | 6/1989 | Hahn et al. . |
| 4,846,154 | 7/1989 | MacAnally et al. . |
| 4,852,551 | 8/1989 | Opie et al. . |
| 4,869,238 | 9/1989 | Opie et al. . |
| 4,878,485 | 11/1989 | Adair . |
| 4,964,710 | 10/1990 | Leiner . |
| 4,969,708 | 11/1990 | Leiner . |
| 4,991,564 | 2/1991 | Takahashi et al. . |
| 4,991,565 | 2/1991 | Takahashi et al. . |
| 5,002,042 | 3/1991 | Okada . |
| 5,025,778 | 6/1991 | Silverstein . |
| 5,050,585 | 9/1991 | Takahashi et al. . |
| 5,088,178 | 2/1992 | Stolk . |
| 5,168,863 | 12/1992 | Kurtzer . |
| 5,188,092 | 2/1993 | White . |
| 5,193,135 | 3/1993 | Miyagi . |
| 5,257,617 | 11/1993 | Takahashi . |
| 5,301,601 | 4/1994 | Nakada et al. . |
| 5,311,990 | 5/1994 | Kalinski ............................ 206/370 |
| 5,402,768 | 4/1995 | Adair ................................ 128/4 |

FOREIGN PATENT DOCUMENTS 0075415  3/1983  European Pat. Off. .

*Primary Examiner*—Richard J. Apley
*Assistant Examiner*—Beverly M. Flanagan

[57] ABSTRACT

The present invention provides an endoscopic sheath for protecting and/or changing an angle of view of an endoscope. The sheath has a distal portion configured to engage a distalmost portion of an endoscope imaging optics. The distal portion houses structure for changing the angle of view of an endoscope. In a preferred embodiment, this structure includes a prism. The distal portion may additionally house structure for changing the angle of illumination of an illumination portion of an endoscope. This structure may be a prism or a curved light guide or at least one angled optical fiber. Both the structure for changing the angle of view of an endoscope and the optical member for changing the angle of illumination of an endoscope may be positioned within the distal portion to align with the respective imaging or illumination elements of the endoscope.

21 Claims, 16 Drawing Sheets

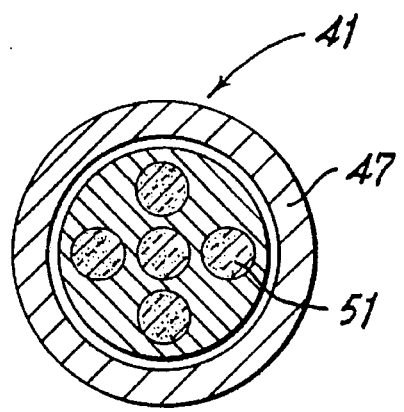
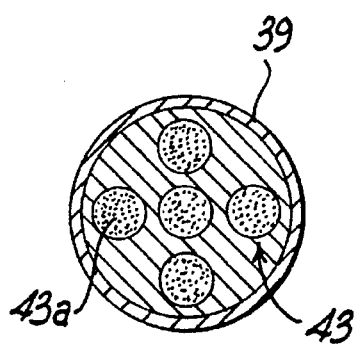
FIG.7  FIG.8
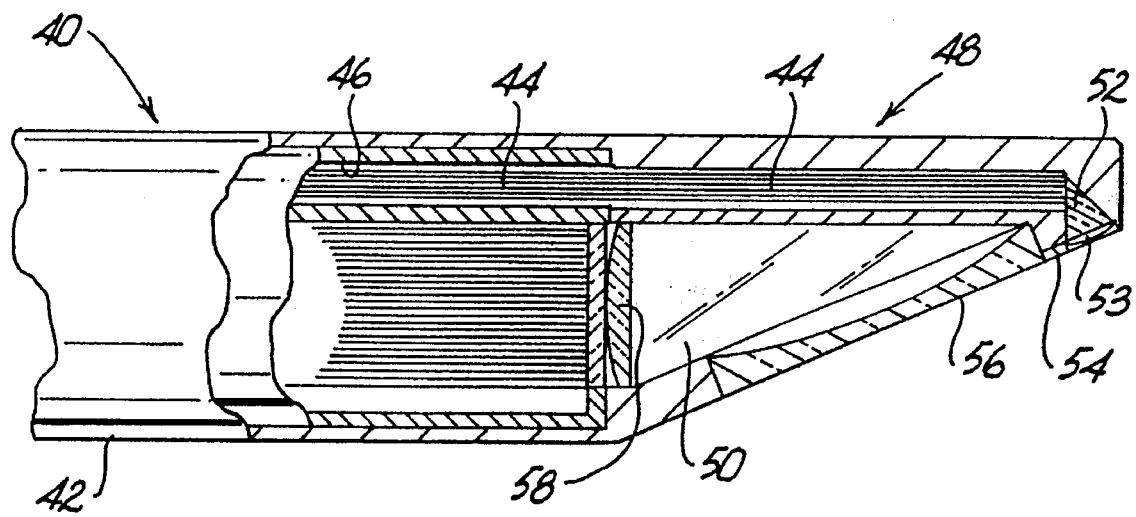
FIG.9
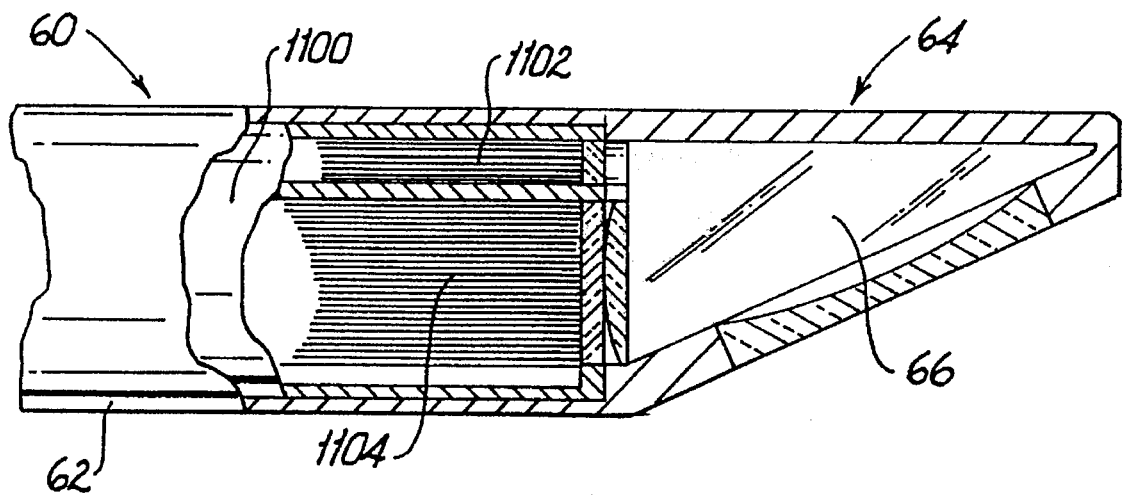
FIG.10

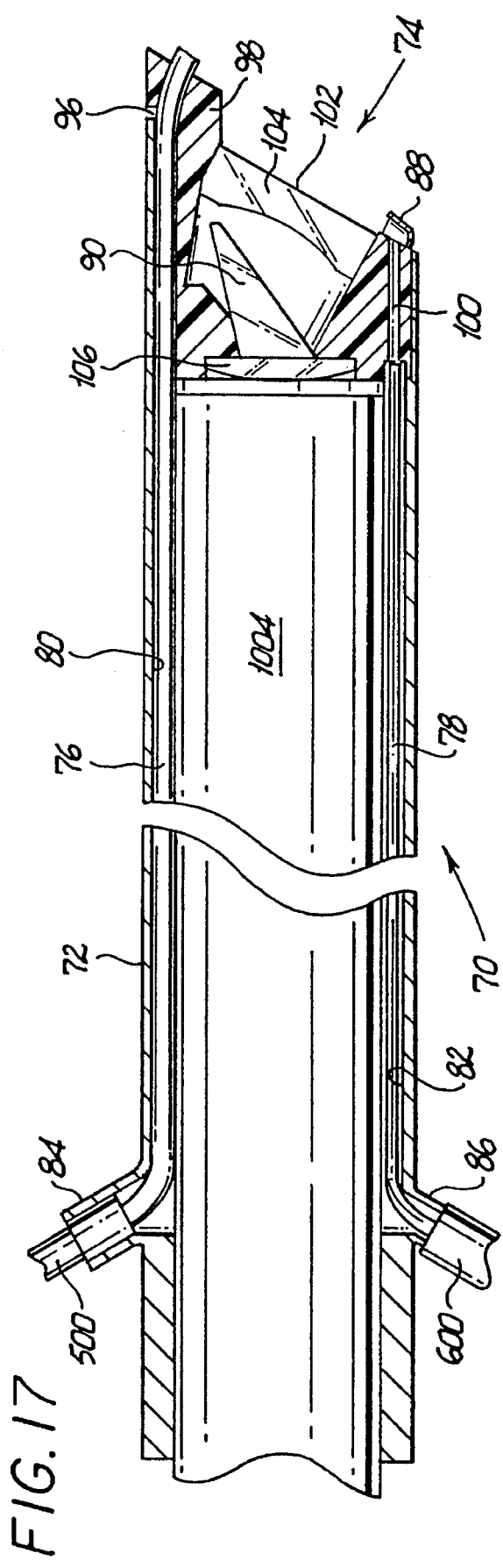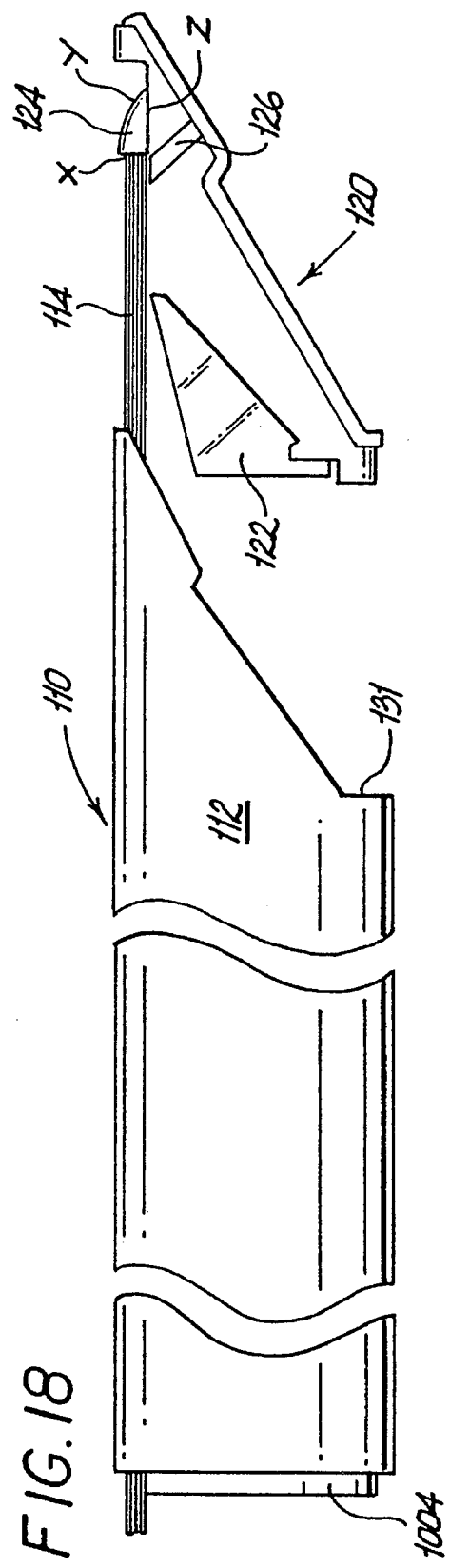
FIG.17
FIG.18

ENDOSCOPE ATTACHMENT FOR CHANGING ANGLE OF VIEW

This is a divisional of U.S. application Ser. No. 08/134,536 field Oct. 8, 1993 pending.

BACKGROUND OF THE INVENTION

1. Field of the Invention

The invention relates to accessories for endoscopes and, more particularly, to endoscope sheaths which change an angle of view of an endoscope.

2. Description of the Related Art

Endoscopes have long been used in surgery to view internal portions of a patient's body from a narrow incision in the body exterior or through a naturally occurring hollow viscus. Endoscopes used for this purpose are long, slender instruments having a shaft which is either rigid or flexible, depending upon the procedure being performed. In general, endoscopes include an objective lens positioned adjacent a distal end, and an image transmission system which may include a fiber optic bundle, relay rods or lenses, or a solid state sensor to transmit the image to the viewer. Endoscopes also are usually equipped with an illumination system, such as a fiber optic bundle, which illuminates the area being imaged.

Generally, a camera adapter is provided at the proximal end of the endoscope to permit the image to be displayed on a monitor for viewing by the entire surgical team. It is also known to provide a fluid and/or gas conduit which permits the surgeon to clean the distal-most imaging lens and/or clear the region in front of the distal-most lens for optical viewing. See, for example, U.S. Pat. Nos. 4,667,656; 4,770,163; and 4,838,246.

Most endoscopes used for medical procedures have a fixed forward viewing angle. Different areas of the body can be imaged by changing the position of the endoscope or, in the case of flexible endoscopes, by bending the distal tip. In these endoscopes, the objective lens is disposed perpendicular to the longitudinal axis of the instrument such that the area directly in front of the instrument is viewed by the user. Other configurations for endoscopes include side-viewing, and oblique angle of view endoscopes.

In certain procedures, in addition to forward viewing endoscopes, it is desirable to have the capability for changing the angle of view during different stages of the procedure. For example, when examining the lining of a body cavity, e.g., esophagus, intestinal walls, it is advantageous to employ a side-viewing or oblique angle of view endoscope. Presently, the ability to view at different angles can only be accomplished by maintaining a variety of expensive high quality reusable side-viewing endoscopes.

It is known in the art to provide attachments which change the angle of view of conventional reusable endoscopes. Typical devices of this type are disclosed in U.S. Pat. Nos. 4,747,661 and 4,787,370. In general, such attachments fit adjacent only the distal end of the endoscope and include complex optical elements which increase the cost of the endoscopes and reduce their efficacy for single-use applications. Additionally, many of the known attachments require special adaptive elements on the distal end of the endoscope in order to properly secure the attachment. The attachments do not cover substantially the elongated endoscopic portion of the endoscope. As a result, it is difficult to clean and re-sterilize the expensive and delicate optics of the endoscope prior to reuse.

Accordingly, it would be advantageous to provide a device which may be readily inserted over or connected to an endoscope and which functions in changing the angle of view of the scope without the need for complex attachments. It would also be advantageous if such device extends substantially the length of the elongated endoscopic portion of the endoscope to protect the endoscope from contamination. It would be a further benefit if the device incorporated an integral illumination and/or irrigation system which provides properly aimed illumination of the area to be viewed and irrigation of the viewing lens surface of the endoscopic sheath and/or the surgical field. It would also be desirable to provide a coupler between a light source and the illumination system which improves the accumulated light by increasing the packing fraction of the fibers at the coupler interface. It would be further desirous if the device could be employed for single use applications.

SUMMARY OF THE INVENTION

Generally stated, the present invention is directed to an endoscopic sheath for protecting and/or changing an angle of view of an endoscope. A distal portion of the sheath houses structure for changing the angle of view of an endoscope. In a preferred embodiment, this structure includes a prism. The distal portion of the sheath may additionally house structure for changing the angle of illumination of the illumination optics portion of an endoscope. This may be a prism, a mirror, a curved light guide, or structure for angling at least one optical fiber. Both the structure for changing the angle of view of an endoscope and the optical member for changing the angle of illumination of an endoscope are positioned within the sheath distal portion to align with the respective imaging or illumination elements of the endoscope.

BRIEF DESCRIPTION OF THE DRAWINGS

Preferred embodiments of the invention are described hereinbelow with reference to the drawings wherein:

FIG. 7 is a cross-sectional view taken along line 7—7 of FIG. 5 showing the glass rods disposed in the coupler;

FIG. 8 is a cross-sectional view taken along line 8—8 of FIG. 5 showing the arrangement of fibers in the light guide;

FIG. 9 is a side view in partial cross-section of the distal end of an endoscope sheath in accordance with a second embodiment illustrating a prism for changing the angle of view, with the illumination system of the endoscope sheath cooperating with the illumination system of the endoscope disposed in the sheath;

FIG. 10 is a side plan view in partial cross-section of an endoscope sheath in accordance with a third embodiment illustrating a prism for changing the angles of view and illumination, and having an endoscope positioned therein;

FIG. 17 is a side cross-sectional view of the elongated sheath portion and prism mount of the endoscope sheath of FIG. 11 illustrating the illumination system and fluid system incorporated in the sheath, and showing an endoscope disposed in the sheath;

FIG. 18 is a side view of an alternative embodiment of the elongated sheath of FIG. 11 incorporating an elongated sheath portion and a prism mount having a 60° prism for altering the angle of view;

DETAILED DESCRIPTION OF THE PREFERRED EMBODIMENTS

Figure 1:
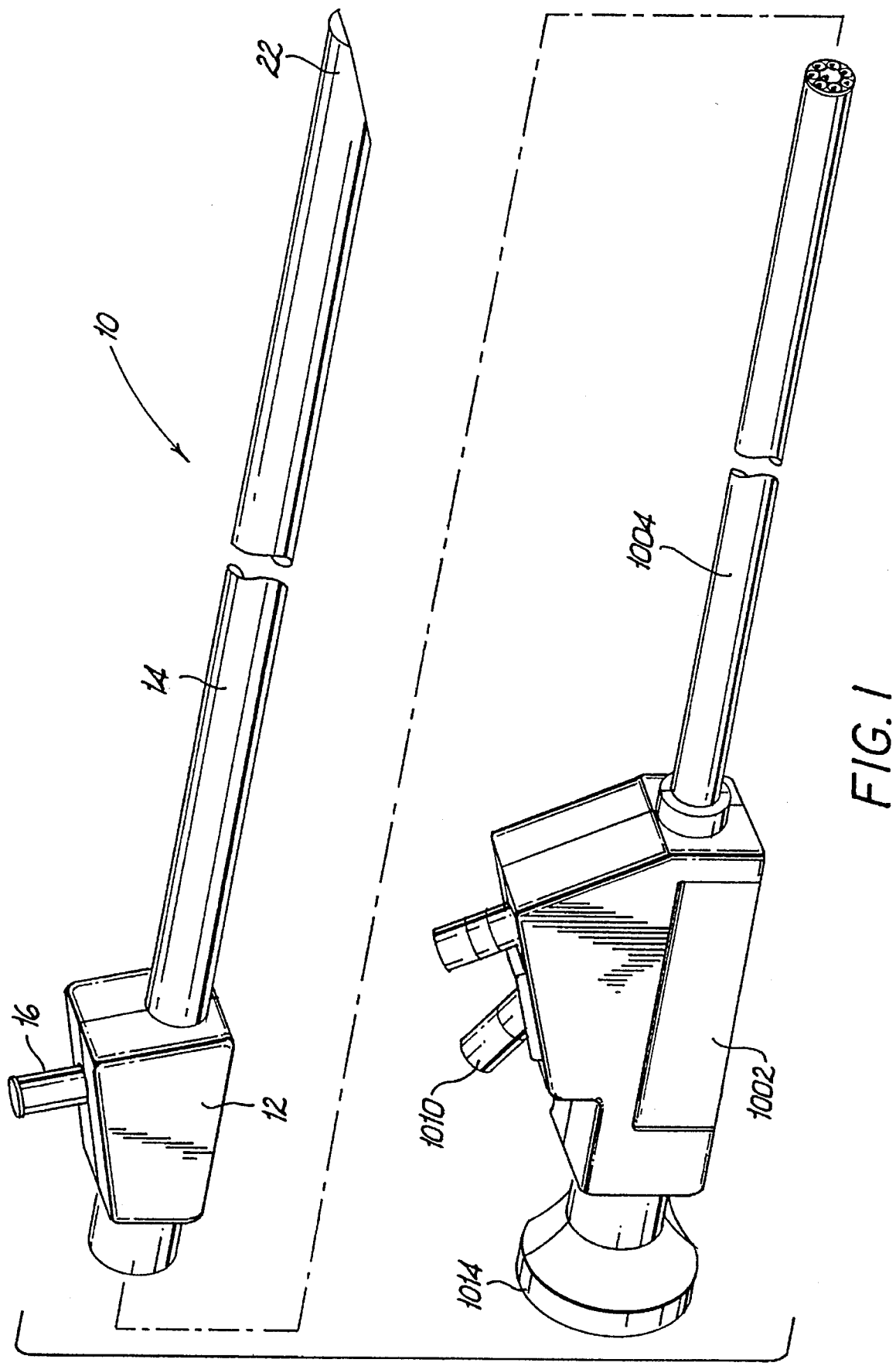
FIG. 1 is a perspective view of an endoscope and an endoscope sheath in accordance with one embodiment of the present invention.

Referring now to the drawings, in which like reference numerals identify similar or identical elements throughout the several views, FIG. 1 illustrates an endoscope sheath in accordance with the principles of the present invention. Endoscope sheath 10 is configured and dimensioned to be positioned over a conventional forward-viewing endoscope 1000 to change the angle of view of the endoscope.

Figure 3:
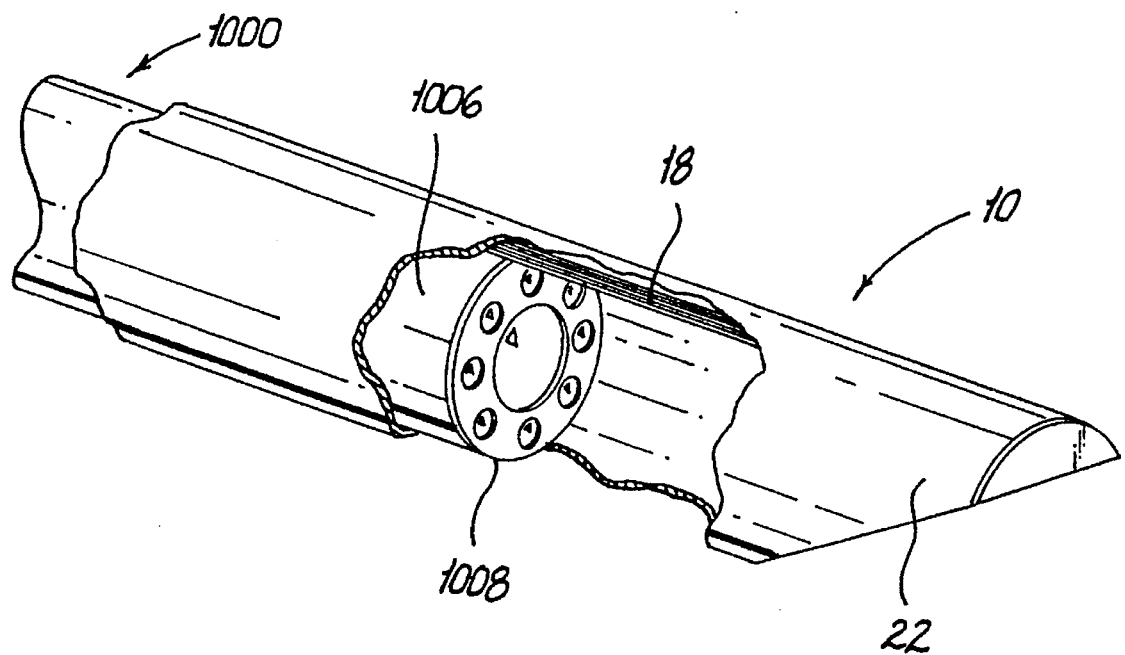
FIG. 3 is a partial perspective view with portions cut away of the endoscope sheath partially mounted to the distal end of an endoscope.

Referring now to FIG. 1, in conjunction with FIG. 3, endoscope 1000 may be any known conventional endoscope and may be either rigid or flexible. The preferred endoscope to be used with endoscope sheath 10 of the present invention includes endoscope housing 1002 and an elongated endoscopic portion 1004 extending distally of the housing 1002. Examples of endoscopes which can readily be utilized with elongated sheath 10 of the present invention are disclosed in U.S. Pat. Nos. 3,089,484; 3,257,902; 4,784,118; 4,964,710 and 5,188,092, the contents of each being incorporated herein by reference. As used herein, "distal" refers to the portion of the endoscope or endoscope sheath furthest from the operator, i.e., in the direction of the endoscopic portion from housing 1002, while "proximal" refers to the portion closest to the operator.

A function of endoscopic portion 1004 is to transfer illuminating light from endoscope housing 1002 to the distal end of the endoscopic portion 1004 to provide illuminating light to the operative site. In an exemplary configuration, endoscopic portion 1004 includes an outer covering 1006 and an annular array of fiber optic elements 1008 extending between proximal illuminating coupling port 1010 of endoscope housing 1002 and the distal end of endoscopic portion 1004 to convey light to the distal end of the endoscope. Preferably, the fiber optic elements 1008 are positioned adjacent the inner wall of the outer covering in an annular configuration as shown in FIG. 3. Any known illumination source may be connected via a light guide 200 (FIG. 2) to coupling port 1010 to provide the illuminating light for the fiber optics 1008. Such illumination sources include, for example, the Lumatec model Superlite light source, halogen lamps, Argon or He—Ne-lasers, tungsten filament incandescent lamps, etc.

Endoscopic portion 1004 incorporates an image transferring system which may include a plurality of fiber optic elements 1012 (FIG. 4) to transfer an image formed at an image plane to eyepiece 1014 of the endoscope (FIG. 1) for viewing. Alternatively, a series of optical lens components may be used instead of fiber optics 1012 to transfer the image to the viewer. Known relay optical systems include those shown and described in U.S. Pat. Nos. 3,089,484; 3,257,902 and the aforementioned 4,964,710. It is also envisioned that a video system including a monitor may be operatively connected to housing 1002, such as by coupling to eyepiece 1014, to provide a video image of the body tissue being viewed. While the preferred embodiments of the present invention will be described in conjunction with an endoscope having a central image transferring system and an annular array of illumination fibers, it will be understood by those skilled in the art that the endoscope sheath could be readily adapted for use with other endoscope configurations such as nonconcentric imaging and illumination optics.

Figure 2:
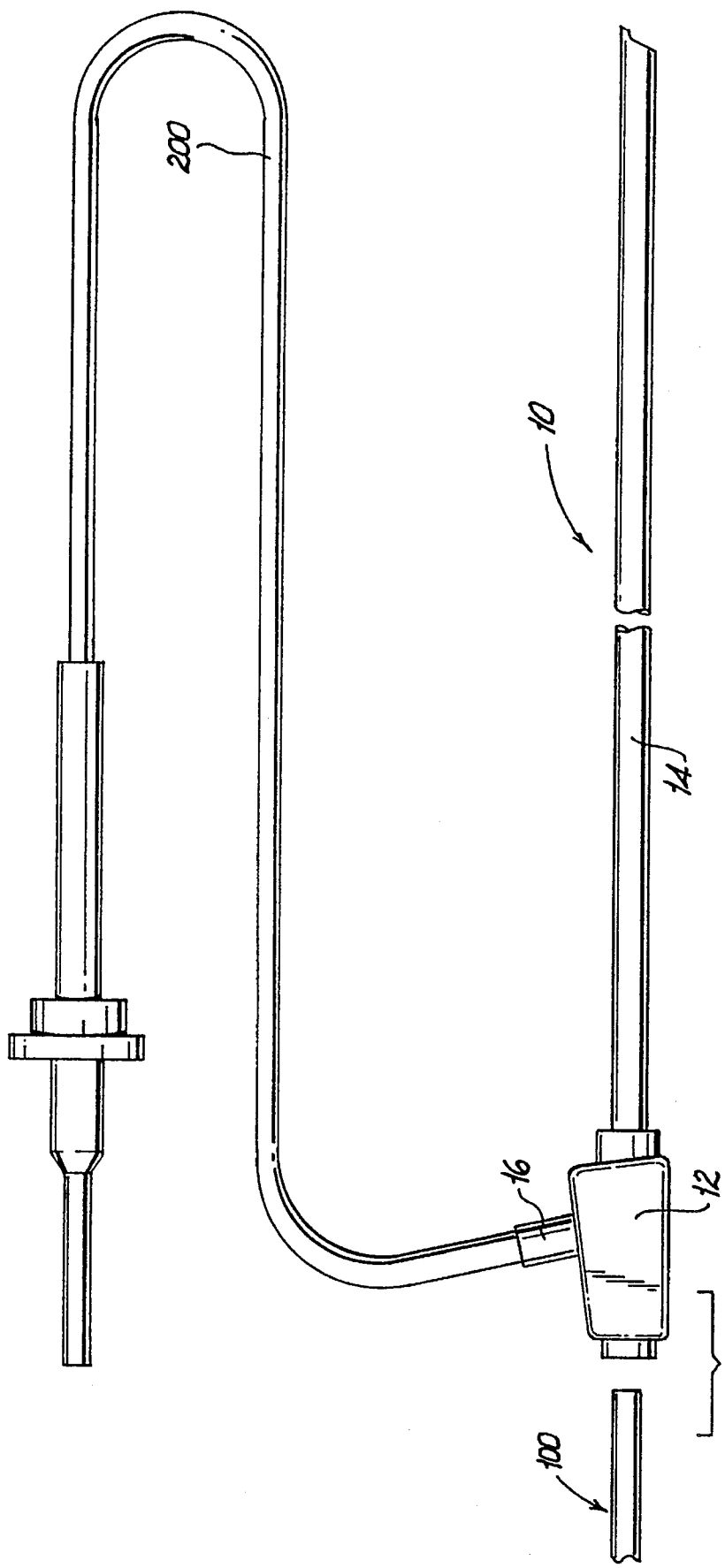
FIG. 2 is a side plan view of the endoscope sheath of FIG. 1 with an illumination light guide, and further with the endoscope sheath axially aligned with an endoscope.

Referring now to FIGS. 1 and 2, in conjunction with FIGS. 3 and 4, the novel endoscope sheath 10 of the present invention will be described in detail. Endoscope sheath 10 includes a housing portion 12 and an elongated sheath portion 14 extending distally from the housing portion 12. Housing portion 12 includes a proximal illuminating inlet connector 16 for reception of a light guide or tube 200 (FIG. 2) which is connected to a light source such as those described above with respect to the endoscope.

Endoscope sheath 10 is preferably of sufficient length to extend over substantially the entire endoscopic portion 1004 of endoscope 1000 to protect and isolate of the endoscope during surgical procedures and prevent direct contact of endoscopic portion 1004 with the body and body fluids. Thus, the user may conveniently switch to and from different angles of view without needing to keep multiple clean endoscopes on hand. Elongated sheath 14 is preferably formed of a sufficiently rigid material such as a biocompatible plastic, stainless steel or the like to be placed over a rigid endoscope. Where the sheath is used with a rigid endoscope the sheath itself need not have considerable rigidity in and to itself since support is provided by the rigid endoscope. The inner diameter of elongated sheath 14 preferably approximates the outer diameter of endoscopic portion 1004 to form a friction fit between the sheath and the endoscope to maintain endoscope sheath 10 on endoscope 1000 during the surgical procedure. In the alternative, the inner portion of elongated sheath 14 of endoscope sheath 10 may be provided with a compressible material having a first non-compressed internal diameter slightly smaller than the outer diameter of the endoscopic portion 1004. Insertion of the endoscopic portion 1004 initially expands the compressible material of elongated sheath 14, which then returns to its original diameter to frictionally engage endoscopic portion 1004. Other means to maintain endoscope 1000 within endoscope sheath 10 can be utilized such as clamps, screws, a bayonet fastener, collets, etc. See, for example, U.S. Pat. No. 5,217,441.

Figure 4:
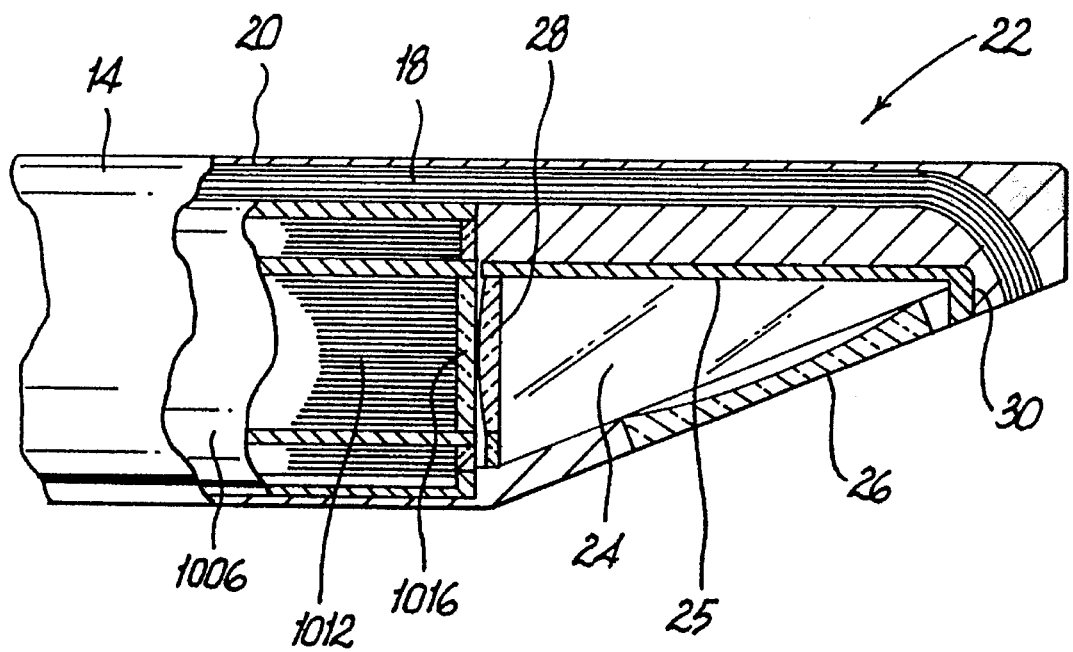
FIG. 4 is a side view in partial cross-section of the distal end of an endoscope sheath in accordance with a first embodiment illustrating the prism for changing the angle of view, as well as an illumination system incorporated into the sheath, and an endoscope disposed in the sheath.

Referring now to FIGS. 2–4, endoscope sheath 10 may also be provided with an illumination system which preferably includes a fiber optic bundle 18 which extends from the inlet connector 16 of housing 12 through a channel 20 (FIG. 4) formed in the wall of elongated sheath 14 to the distal end portion 22 of the elongated sheath 14. Optical fiber bundle 18 may be fabricated from any suitable optical material including glass and optical plastics. A preferred material for optical fiber 18 is polymethyl methacrylate (PMMA) having a relatively large numerical aperture to provide a field of illumination equal to or greater than the angled field of view. The integral illumination system of endoscope sheath 10 enables the surgeon to alter the illumination angle to illuminate the new, angled area to be viewed independent of the illumination system of the endoscope. Further details of the illumination system are discussed below. As will be appreciated, where the sheath contains a separate illumination system, the endoscope used therewith need not contain a second illumination system. Thus, it is contemplated that the sheath could be used with an endoscope having only an imaging optical system without an illumination optical system.

Referring to FIG. 4, the distal end portion 22 of elongated sheath portion 14 houses the optical elements used to change the angle of view of the endoscope. In general, these optical elements include an optical member 24 which cooperates with imaging portion 1012 of the endoscope 1000 to change the angle of view of the imaging portion. In this embodiment, optical member 24 comprises a 30° deflection prism used to change the direction of view of endoscope 1000 from forward-viewing to viewing at an oblique angle, i.e., at a 30° angle relative to the longitudinal axis of endoscope 1000. In a preferred embodiment, prism 24 is a hybrid prism, i.e., one which principally reflects light, but, also refracts the light so as to change the angle of view. In the alternative and depending on the particular application, prism 24 may be a full reflection prism or a full refraction prism. A full refraction prism is preferably used when it is desirable to change the angle of view less than about 30° relative to the endoscopic axis since such refraction prisms may introduce undesirable aberrations, e.g., chromatic aberration, when used as the sole means for changing the angle of view. Reflecting surface 25 of prism 24 may be a metalized mirror having an aluminum base which is coated with at least one layer of silicon dioxide and possibly one or more coats of black paint to protect the metalized layer.

The optical components of distal end portion 22 of endoscope sheath 10 also includes a concave lens 26 which is positioned between prism 24 and the area to be viewed. Lens 28 assists in directing the incident rays through optical member 24 and acts as a window, sealing the prism from the external environment. A convex lens 28 is positioned between optical prism member 24 and objective lens 1016 disposed at the distal end of the endoscope image transferring system 1012. Concave lens 26, prism 24 and convex lines 28 couple the image into the endoscope which maintaining the field of view, albeit at an altered angle. Preferably, the optical components are arranged in an afocal system thus avoiding the need for refocusing of the instrument. Although depicted in FIG. 4 as two separate elements, optical member 24 and convex lens 28 may alternatively be formed as a single element, e.g., as a prism having a proximal surface portion configured as a convex lens. The optical components of endoscope sheath 10 may be fabricated from suitable optical materials such as glass or optical plastics.

Fiber bundle 18 of the illumination system of endoscope sheath 10 is curved downwardly at its distal end towards the center axis of elongated sheath 12 to orient the tips of the illumination fibers to provide uniform illumination to the angled field of view. Such orientation of fiber bundle 18 alters the angle of illumination from a position at substantially 0° relative to the longitudinal axis of the endoscope 1000 to an angle of about 30° relative to the axis to correspond to the angle of view provided by prism 24. Accordingly, the area to be viewed will be directly illuminated by the illumination system. Further, it is preferable to provide for an opaque barrier, such as barrier sheath portion 30 to separate the curved distal end of fiber bundle from the optical components 24, 26. Barrier portion 30 reduces veiling glare by disposing the illumination outlet distal to and offset from the imaging optics.

Referring now to FIGS. 5–8, there is illustrated an alternative embodiment of the endoscope sheath of the present invention. Endoscope sheath 31 includes housing portion 33 and an elongated sheath portion 35 extending distally from the housing portion 33. Elongated sheath 35 is dimensioned to extend over substantially the entire endoscopic portion of an endoscope of the type described in connection with the embodiment of FIG. 1.

A light guide 37 is integrally formed with endoscope sheath 31 through housing portion 33 and includes a fiber optic light guide tube 39 and light source coupler 41 attached to one end portion of the guide tube 39. Light guide tube 39 includes an optical fiber bundle 43 (FIGS. 6 and 8) having a plurality of individual optical fibers 43a which extend through the length of the tube and into proximal housing portion 33 of endoscope sheath 31 where the fibers extend to the distal end portion 45 of elongated sheath 35.

The optical fibers 43a of fiber bundle 43 are arranged in a clover leaf configuration as shown in FIG. 8 within light tube 39. The optical fibers 43a are arranged in a side by side configuration (similar to the configuration of optical fibers 18 in FIG. 3) and through a channel formed in the wall of elongated sheath 35 to the distal end portion 45 of endoscope sheath 31. Preferably, optical bundle 43 includes 5 optical fibers however any number of fibers may be used depending on the application and design specifications. The fibers preferably are fabricated from polymethylmethacrylate (PMMA) and have a fluorinated polymer cladding. The diameter of each fiber is about 1.5 mm.

Figure 5:
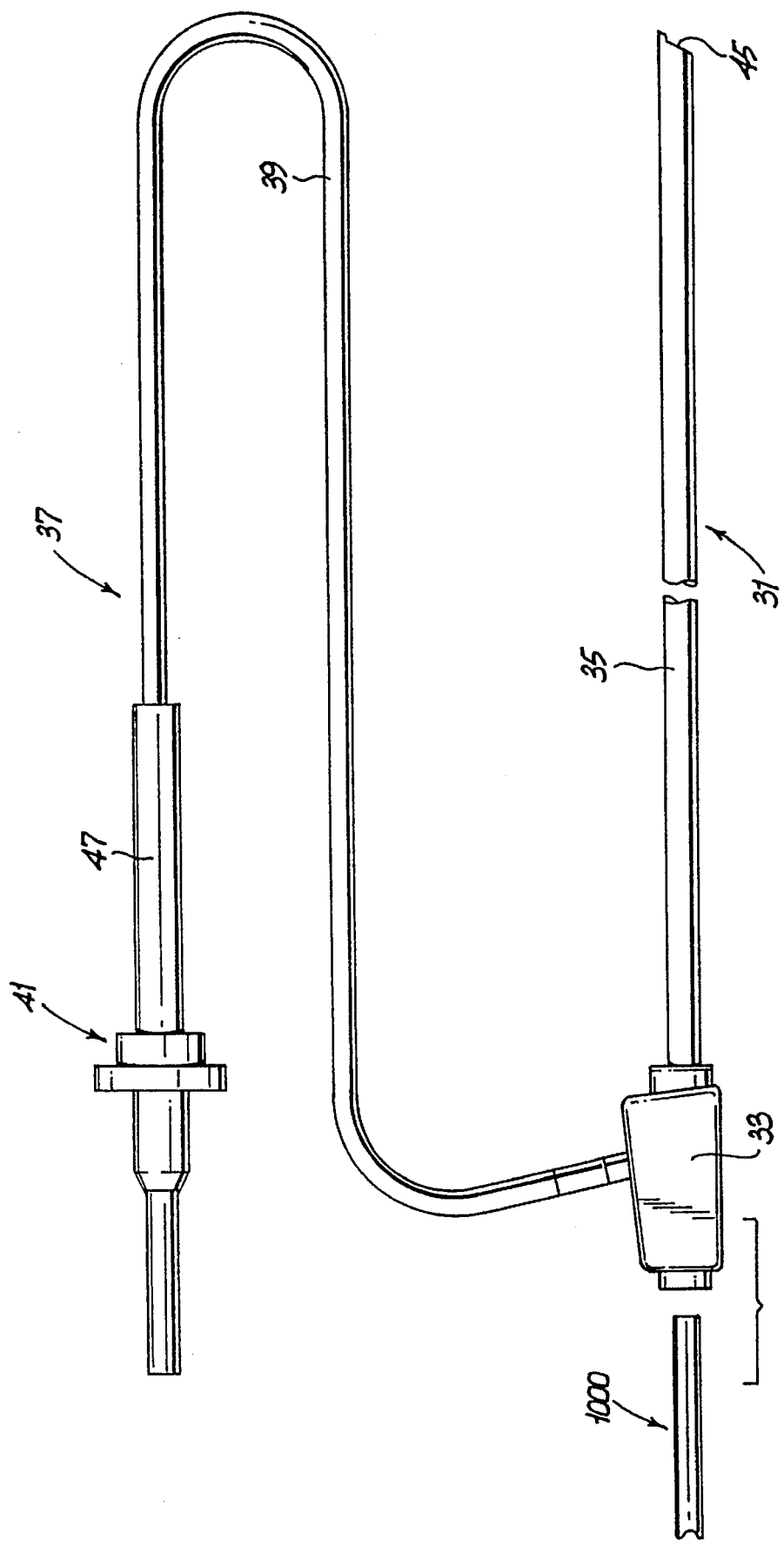
FIG. 5 is a side plan view of a sheath in accordance with the present invention having an integral light guide and coupler extending proximally therefrom.
Figure 6:
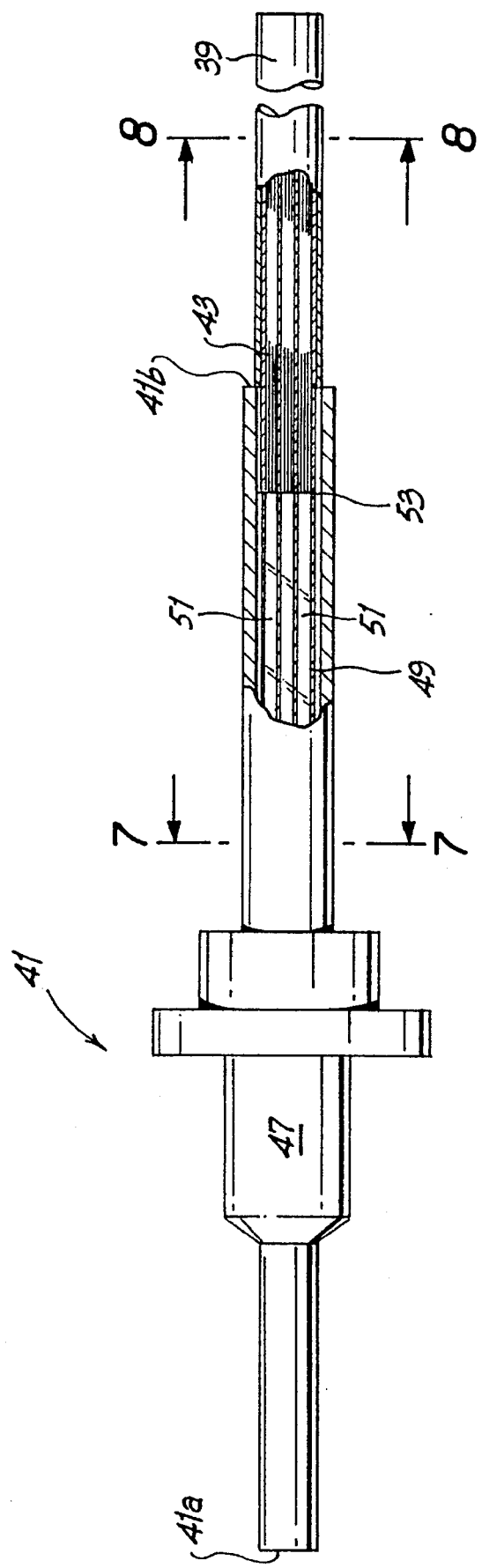
FIG. 6 is an enlarged side view of the coupler in accordance with a preferred embodiment of the present invention.

Referring particularly to FIGS. 6 and 7, in conjunction with FIG. 5, light guide coupler 41 includes coupler housing 47 which is fabricated from a metallic material such as aluminum. Coupler housing 47 includes a plurality of longitudinal bores 49 extending completely therethrough which are formed by a drilling or boring operation. Alternatively, the coupler with a bore, could be extruded from any suitable heat resistant material, such as, metal, ceramic or heat resistant plastic. Longitudinal bores 49 house a plurality of cylindrically shaped glass rods 51 which extend from light source inlet end portion 41a of coupler 41 to a position identified by reference numeral 53 intermediate the inlet end 41a and light tube coupler end 41b of the coupler. The remaining portion of coupler housing 47 defined between position 53 (FIG. 6) and light tube coupler end 41b accommodates the ends of optical fibers which extend beyond light tube 39. In particular, the size and number of glass rods preferably correspond identically with the size and number of fibers in the fiber optic bundle. A single optical fiber 43a is positioned within each longitudinal bore 49 of coupler housing 47 such that each single fiber 43a is in face to face contacting relation with a single glass rod 51 at position 53. Optical bundle 43 may be secured within coupler 41 by conventional means. Specifically a heat resistant adhesive or friction fit is preferred.

Figure 6A:
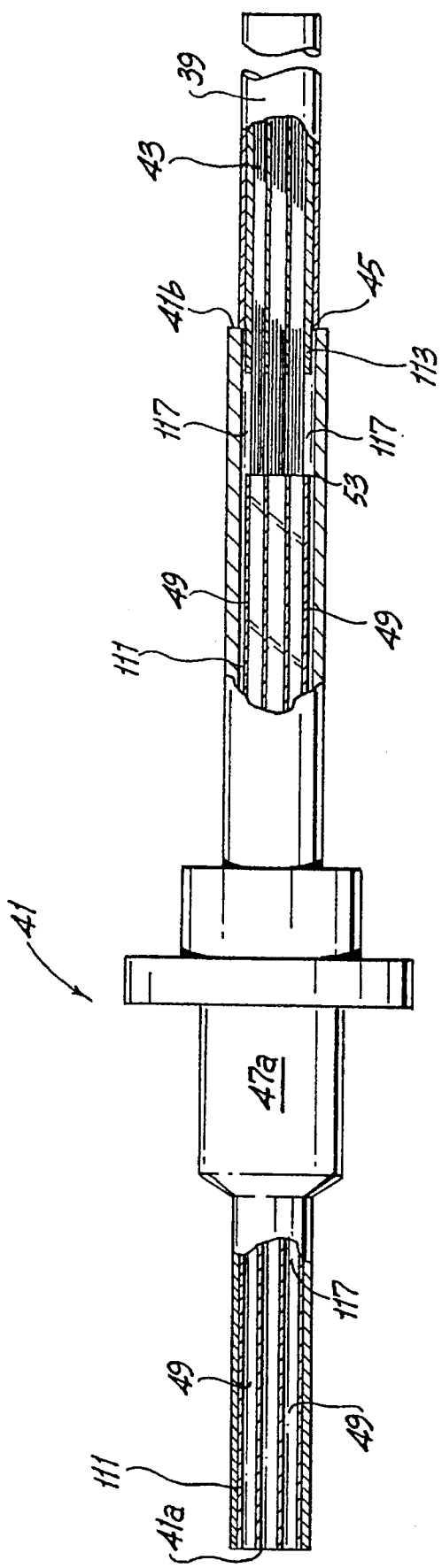
FIG. 6A is an enlarged side view of an alternative coupler in accordance with the present invention.

FIG. 6A shows an alternative preferred coupling 47a configured substantially similar to coupling 47 of FIG. 6 with the exception of inner bore 119. In this embodiment, inner bore 119 is substantially circular in cross-section and dimensioned to receive a pair of glass rod mounting sleeves 111 and a fiber optic mounting sleeve 113 therein. Preferably, both the glass rod mounting sleeve 111 and fiber optic mounting sleeve 113 are fabricated from an engineering metal or plastic and are spaced apart so as to inhibit the conduction of heat longitudinally through coupling 47a. The fibers 43a of the fiber optic bundle 43 extend proximally of fiber optic mounting sleeve 113 and are positioned in abutment with glass rods 49. This configuration establishes air gaps 117 between sleeves 111 and 113 which inhibit heat conduction to fibers 43a.

The face to face arrangement of glass rods 51 and optical fibers 43a within the longitudinal bores of coupler housing 47 increases the coupling efficiency of the fibers 43a and glass rods 51, which thereby results in a high transmittance of light from the glass rods to the optical fibers with minimal light loss. For example, in a seven-fiber fiber optic bundle system the relative output of a system with this arrangement of fibers and glass rods was at least double that of conventional fiber optic systems having a high number of fibers and better than conventional liquid systems.

Glass rods 51 are preferably fabricated from a heat resistant material such as clad glass rods, i.e., glass rods having a (glass) cladding with a lower index of refraction than that of the core glass material. Such clad glass rods are available from Electro Fiber Optics. Preferably, the diameter of each glass rod 51 is identical to the diameter of each individual optical fiber 43a, i.e., about 1.5mm. Also, in the preferred embodiment, 5 glass rods 51 are provided to supply light to the five individual optical fibers 43a of optical bundle 43.

Referring now to FIG. 9, there is illustrated an alternative embodiment of the endoscope sheath of the present invention. Endoscope sheath 40 is similar in most respects to endoscope sheath 10 of FIGS. 1–4 and includes an elongated sheath portion 42 extending from a housing portion (not shown) and having incorporated therein an integral illumination system in the form of a fiber optic bundle 44 which extends through a channel 46 formed in sheath portion 42. In this embodiment, the distal end portion 48 of endoscope sheath 40 employs a 60° deflection prism element 50 to alter the angle of view 60° relative to the axis of the endoscope. in addition, at the extreme distal end portion 48 of the elongated sheath 40 at a position adjacent the distal end of fiber optic bundle 44 is a prism element 52. Prism element 52 changes the angle of illumination from substantially 0° relative to the endoscope axis to 60° relative to the endoscope axis to correspond to the 60° angle of view. Thus, the oblique area to be viewed is directly illuminated by the illumination system. A concave lens 53 may be disposed adjacent prism 52 and functions in diverging the light rays passing through prism 52 to increase the area of the body cavity illuminated by fiber optic bundle 44. An opaque barrier portion 54 is present between the distal light emitting end of fiber bundle 44 and prism 50 to reduce veiling glare. Distal end portion 48 also includes a concave lens 56 and convex lens 58 which function in a similar manner to their corresponding components described in connection with the embodiments of FIGS. 1–4.

FIG. 10 illustrates an alternate embodiment of the endoscope sheath of the present invention. Endoscope sheath 60 includes an elongated sheath portion 62 which is positioned over endoscope 1100 having illumination system 1102 in the form of fiber optic bundles. Endoscope sheath 60 does not have an independent illumination system as the prior two embodiments. Endoscope sheath 60 includes an elongated sheath portion 62 and a distal end portion 64 connected to the sheath portion 62. Distal end portion 64 includes an optical element 66 which changes both the angle of view of the imaging system 1104 of the endoscope 1100 and for changing the angle of illumination of the illumination portion 1102 of the endoscope. Element 66 is a prism which aligns with both the imaging system 1104 and the illumination portion 1102 of endoscope 1100 and can direct/reflect light for illumination and imaging at substantially the same angle to the longitudinal axis.

Referring now to FIGS. 11, 12, 13A, 13B and 14—17, there is illustrated another alternative embodiment of the present invention. Endoscope sheath 70 includes an elongated sheath member 72 and a prism mount 74 which is adapted to be mounted to the distal end portion of elongated sheath member 72. Elongated sheath 72 is to be positioned over the endoscopic portion 1004 of the endoscope 1000 and includes an illumination system in the form of fiber optic bundle 76 and a fluid and/or gas conduit 78 which extends along the length of the sheath member 72. As illustrated in FIG. 17, fiber optic bundle 76 and conduit 78 extend through channels 80, 82 respectively formed in a wall of sheath member 72. An illumination inlet connector 84 at the proximal end of sheath member 72 receives an illumination guide tube 500 extending from a light source to supply the fiber optic bundle 76 with light. An inlet port 86 is also formed on the proximal end portion of the elongated sheath 72 and receives a fluid supply tube 600. The fluid mechanism includes an outlet port or nozzle 88 which directs over and/or is in front of the distalmost lens surface 102 of prism mount 74 to clean the lens surface so as to remove body fluids which may accumulate thereon during the surgical procedure and/or to clear the region in front of the lens to enhance viewing.

Figure 12:
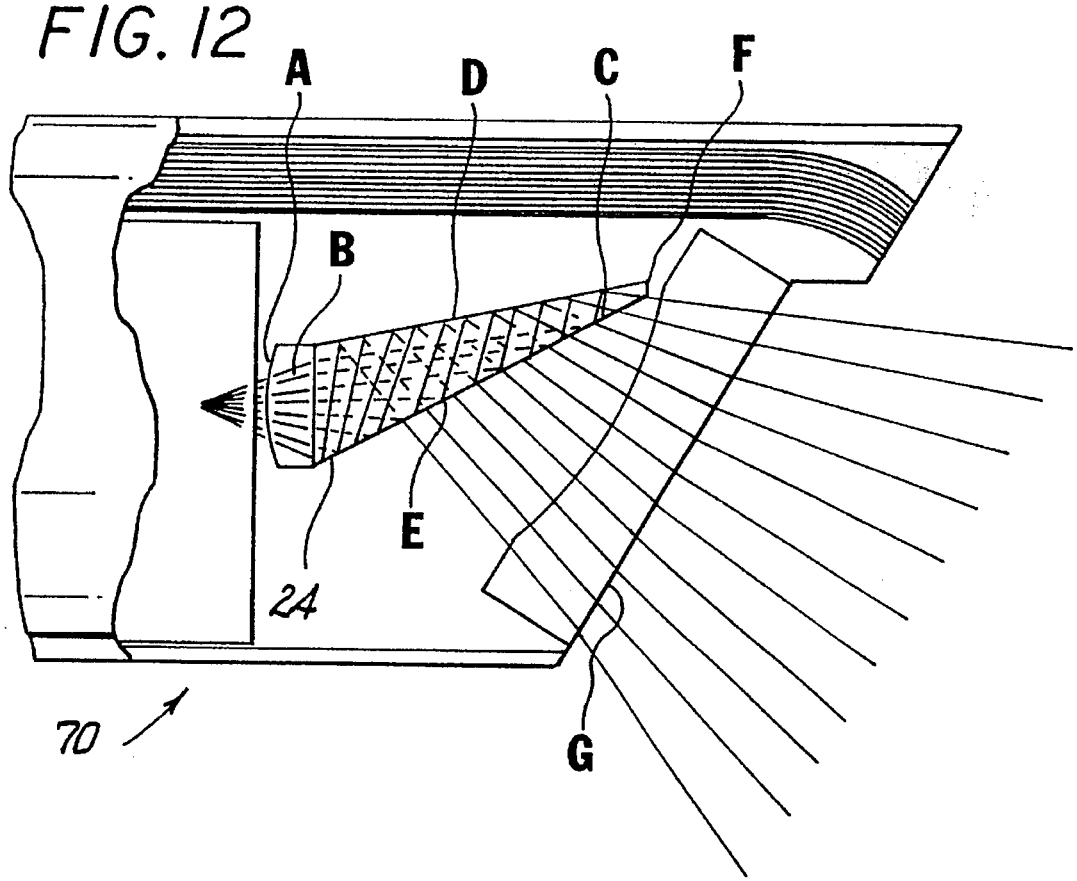
FIG. 12 is a side schematic view in partial cross-section of the distal end of the endoscope sheath illustrating ray path and orientation through the prism of the endoscope sheath.

The novel prism mount 74 is adapted to be positioned within and attached to the distal end portion of the sheath member 72. Prism mount 74 preferably defines an outer diameter which is substantially equal to or slightly less than the inner diameter of the distal end of sheath member 72 to form a frictional fit between the two components to thereby mount the prism mount 74 to the sheath member. Adhesives and/or sealing compounds may be used to secure the prism mount to the sheath member and to seal the distal end of the sheath. Prism mount 74 includes a 30° hybrid prism 90 for changing the angle of view approximately 30° relative to the axis of the endoscope. FIG. 12 illustrates the ray path and orientation through the optical elements of prism mount 74. The geometrical characteristics of the optical components of prism mount 74 are defined by lens surfaces A–F as shown in FIG. 12. The on-axis geometrical and optical parameters of the optical components of optical sheath 70 are recorded in Table 1 below. Table 1 is a follows:

TABLE 1

| Surface | Radius | Thickness | Medium | Index |
|---|---|---|---|---|
| A | 0.488 | 0.035 | Bk7 | 1.52 |
| B | Plano | N/A | F2 | 1.62 |
| C | Plano | N/A | F2 | 1.62 |
| D | Plano | N/A | F2 | 1.62 |
| E | Plano | .081 | AIR | 1.00 |
| F | 0.371 | .087 | [1]Epoxy | 1.56 |
| G | Plano | | | |

*dimensions are in inches
[1]Emerson & Cuming Stycast 1267 Epoxy

Figure 13A:
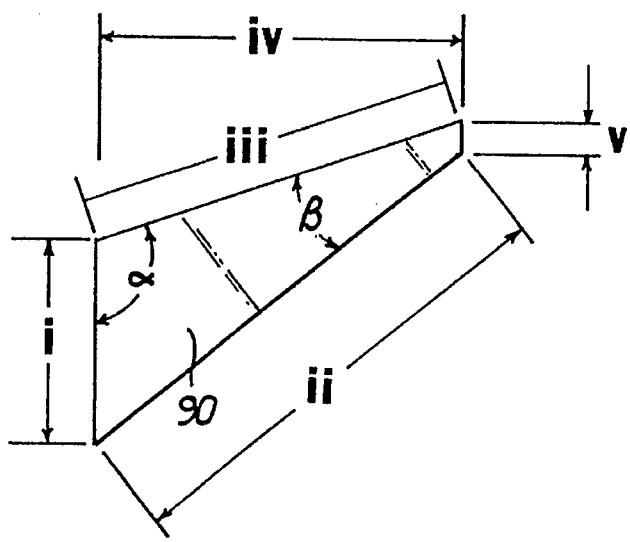
FIGS. 13A and 13B are side and frontal views respectively of the 30° deflection prism of FIG. 12.
Figure 13B:
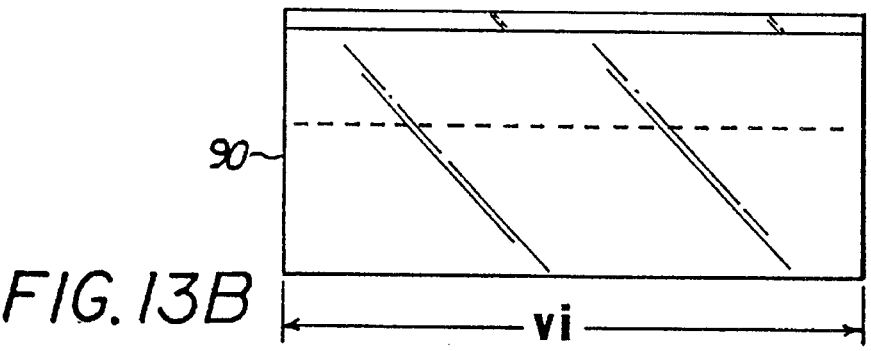
Figure 14:
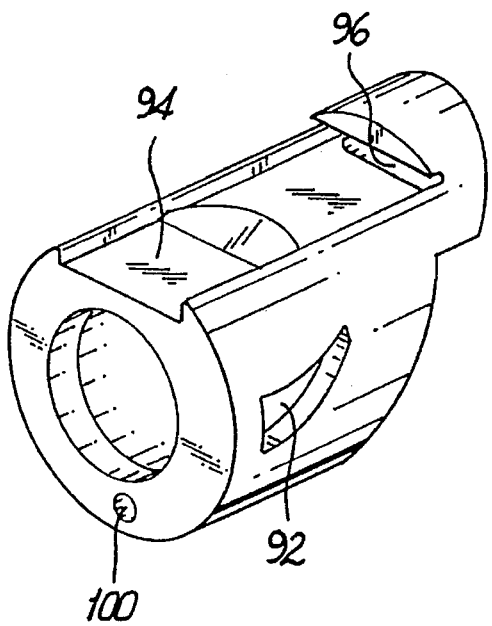
FIG. 14 is a perspective view of the prism mount of FIGS. 11.
Figure 15:
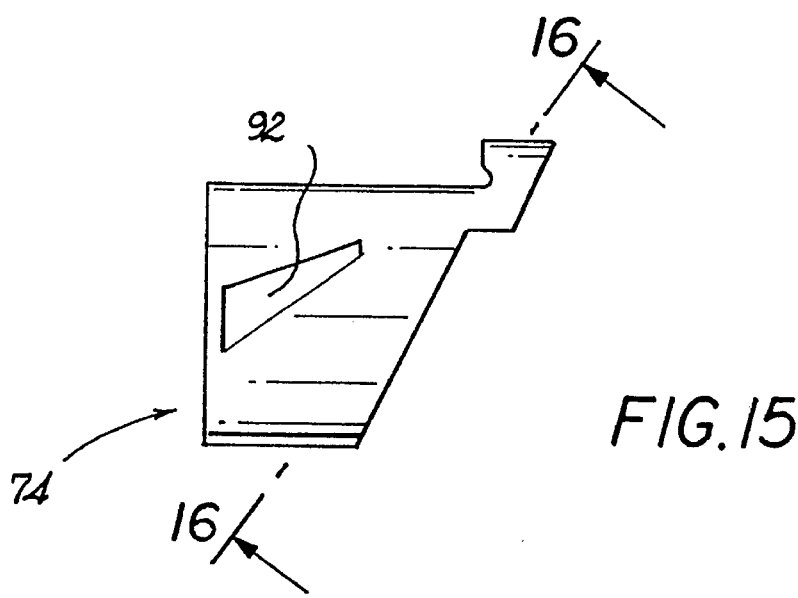
FIG. 15 is a side view of the prism mount of FIG. 14.
Figure 16:
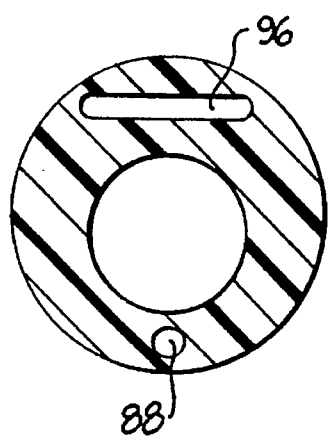
FIG. 16 is a cross-sectional view taken along the lines 16—16 of FIG. 15.
Figure 19:
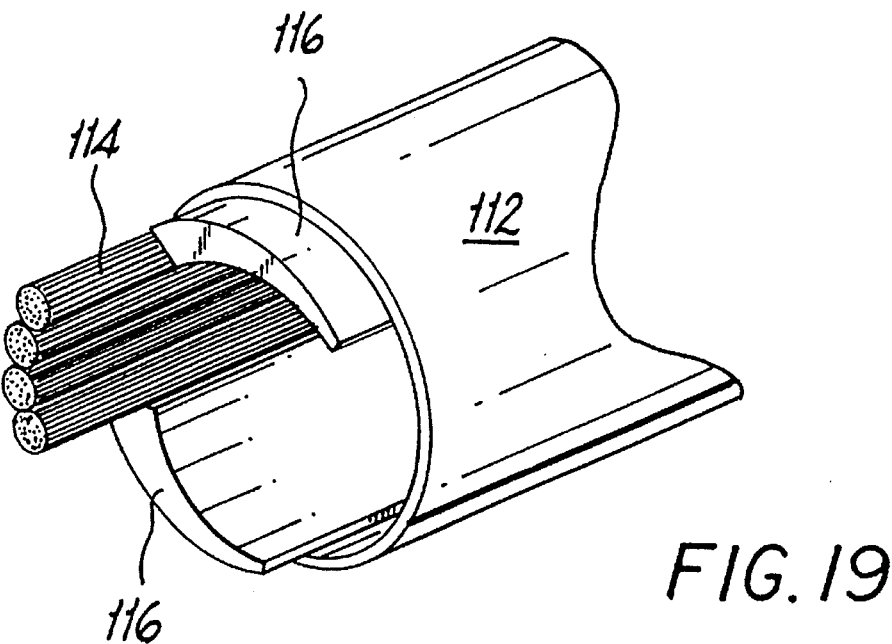
FIG. 19 is a perspective view of the proximal end portion of the elongated sheath of FIGS. 11 and 18 illustrating alignment inserts incorporated therein to properly align the elongated sheath when positioned over the endoscope.

FIGS. 13A and 13B illustrate the specific dimensions and angles of a preferred 30° hybrid prism in accordance with the invention. Table 2 below outlines these dimensions in detail. Table 2 is as follows:

TABLE 2

| Surface or Angle | Dimension | Angle (degrees) |
|---|---|---|
| i | 0.117 | N/A |
| ii | 0.304 | N/A |
| iii | 0.253 | N/A |
| iv | 0.240 | N/A |
| v | 0.011 | N/A |
| vi | 0.387 | N/A |
| α | N/A | 108°46' |
| β | N/A | 19°12' |

*dimensions are in inches

Prism 90 is preferably inserted within a correspondingly dimensioned opening 92 (FIGS. 14–16) formed in the wall of prism mount 74 and secured within the prism mount by snap fit or other friction fit, adhesives or the like. The upper portion of prism mount 74 defines a recessed region 94 which is dimensioned to accommodate the optical fibers 76 extending from elongated sheath member 72. Prism mount 74 also includes angled channel 96 adjacent recessed region 94 which accommodates the extreme distal end of the optical fibers 76. Channel 96 bends the fibers towards the longitudinal axis of endoscopic portion 1004 to alter the illumination angle in a manner similar to that described in connection with the embodiments of FIGS. 1–4, i.e., channel 96 redirects optical fibers 76 such that the light rays are directed from prism mount 74 at a 30° angle relative to the axis of the endoscope. The barrier portion 98 (FIG. 17) defined between channel 96 and the optical components of prism mount 74 minimizes veiling glare in a manner similar to that described above. Prism mount 74 may also contain a channel 100 which receives the distal end of fluid conduit 78. Channel 100 terminates in nozzle 88 which directs fluid over and/or in front of lens surface 102 to clean the lens surface and/or clear the region in front of the lens for optimal viewing. The remaining optical components of prism mount 74 include concave lens 104 positioned at the distal end of prism mount 74 and having lens surface 102, and convex lens 106 disposed at the proximal end surface of prism 88. Lens 102 and lens 106 function in a similar manner to their corresponding lenses of the embodiment of FIGS. 1–4. Sealants may be used to seal the distal end of the sheath, such as at fibers 76 and conduit 78.

Figure 11:
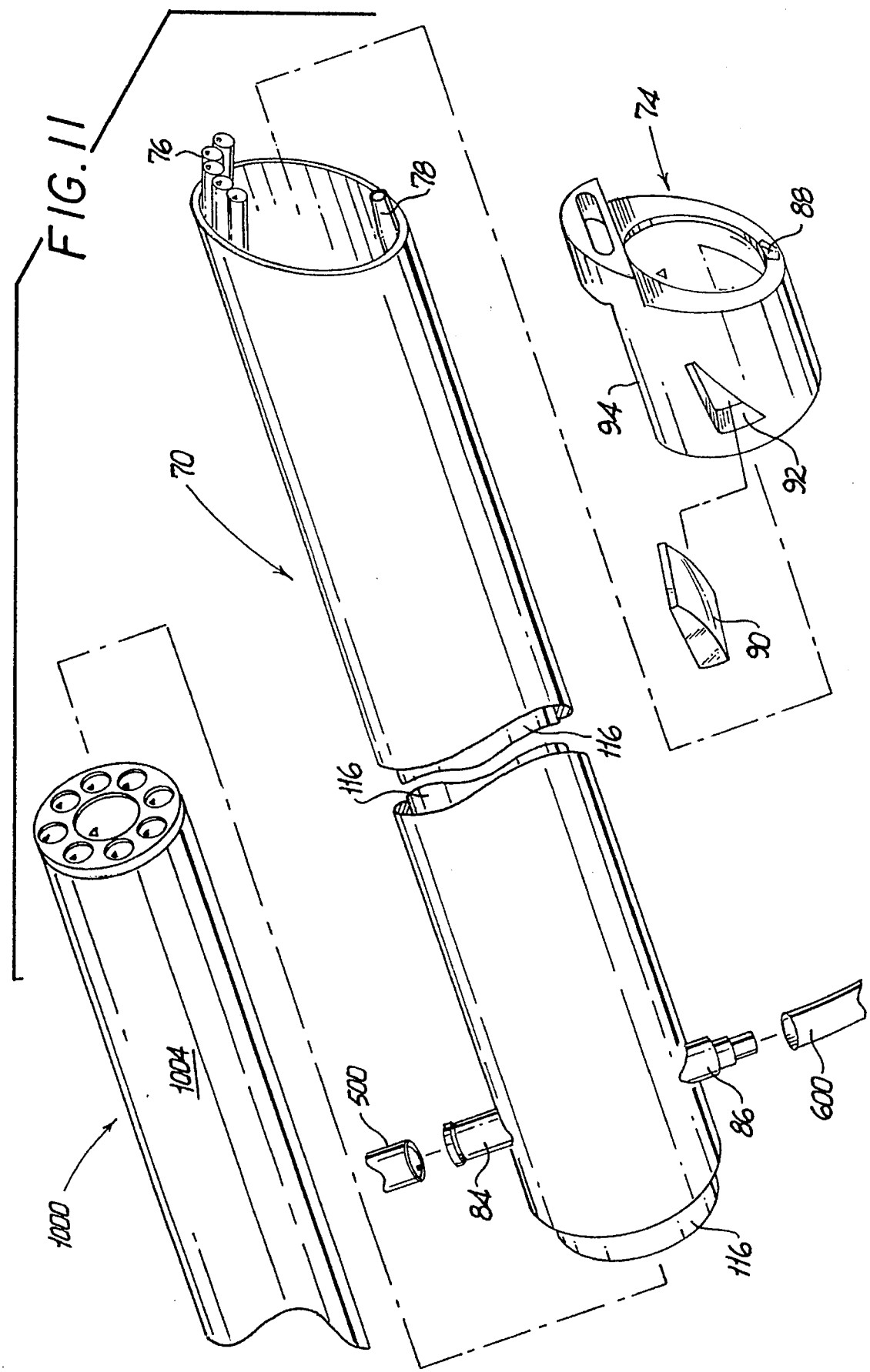
FIG. 11 is an exploded perspective view with parts separated of a fourth embodiment of the endoscope sheath of the present invention incorporating an elongated sheath portion and a prism mount having a 30° prism for altering the angle of view.

Referring now to FIGS. 18–21, there is illustrated another alternative embodiment of the present invention. Endoscope sheath 110 is similar to the endoscope sheath described in connection with the embodiment of FIGS. 13–17 and includes an elongated sheath 112 having an fiber-optic bundle illumination system 114. Elongated sheath 112 includes aligning insert members 116 (FIG. 19) disposed within the interior of sheath 112. Insert members 116 may extend along the length of elongated sheath 112 and are dimensioned to reduce the effective inner diameter of elongated sheath 112 to approximate the outer diameter of endoscopic portion 1004. Insert members 116 may also serve to form a friction fit between the sheath 110 and the endoscope portion 1004. Aligning inserts 116 also define a channel 118 to accommodate the fiber optic bundle 114. See FIG. 19. Similar inserts are shown in FIG. 11. It is contemplated that the elongated sheath and alignment inserts could be integrally molded together as one piece to reduce cost and facilitate assembly. It is also contemplated that the plurality of illumination fibers in the sheath may be replaced by a light transmissive solid molded plastic light guide conforming to the shape of the illumination channel in the sheath, or a liquid-containing light guide similarly conforming to the light channel.

Prism mount 120 includes a 60° prism 122 which is mounted within the prism mount 120 for changing the angle of view 60° relative to the longitudinal axis of the endoscope. Prism 122 includes wing portions 123 (FIG. 21) disposed on opposing side walls thereof which engage flanges 125 of prism mount 120. Because the distal tip of the prism is captured in notch-forming tabs on the mount the notch-forming tabs, wing portions and flanges securely hold prism 122 to the mount. Prism mount 120 also includes a light guide 124 which may be integrally formed with prism mount 120 and disposed adjacent the distal end of fiber optic bundle 114. Light guide 124 alters the angle of illumination 60° relative to the axis of the endoscope without requiring bending of the fiber optic bundle 114. Light guide 124 preferably has a total internal reflection surface Y for directing illumination from the fibers toward the angled field of view. Prism mount 120 also includes an opaque barrier 126 (FIG. 20A) positioned between light guide 124 and prism 122. The barrier 126 comprises a reflective or opaque layer such as foil which fits into channel 127 between prism 122 and light guide 124 and extends proximally to the overlap mirrored surface of prism 122. Barrier 126 minimizes veiling glare and leakage of light between prism 122 and light guide 124.

Figure 20A:
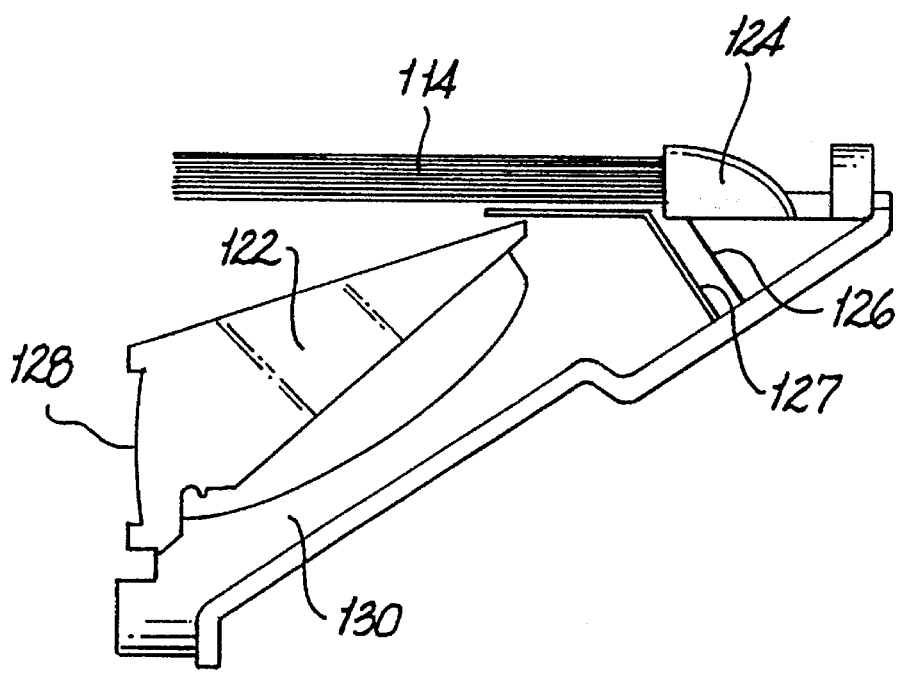
FIG. 20A is a side plan view of the prism mount of FIG. 18 illustrating the positioning of the optical fiber of the elongated sheath portion with respect to the prism mount.
Figure 20B:
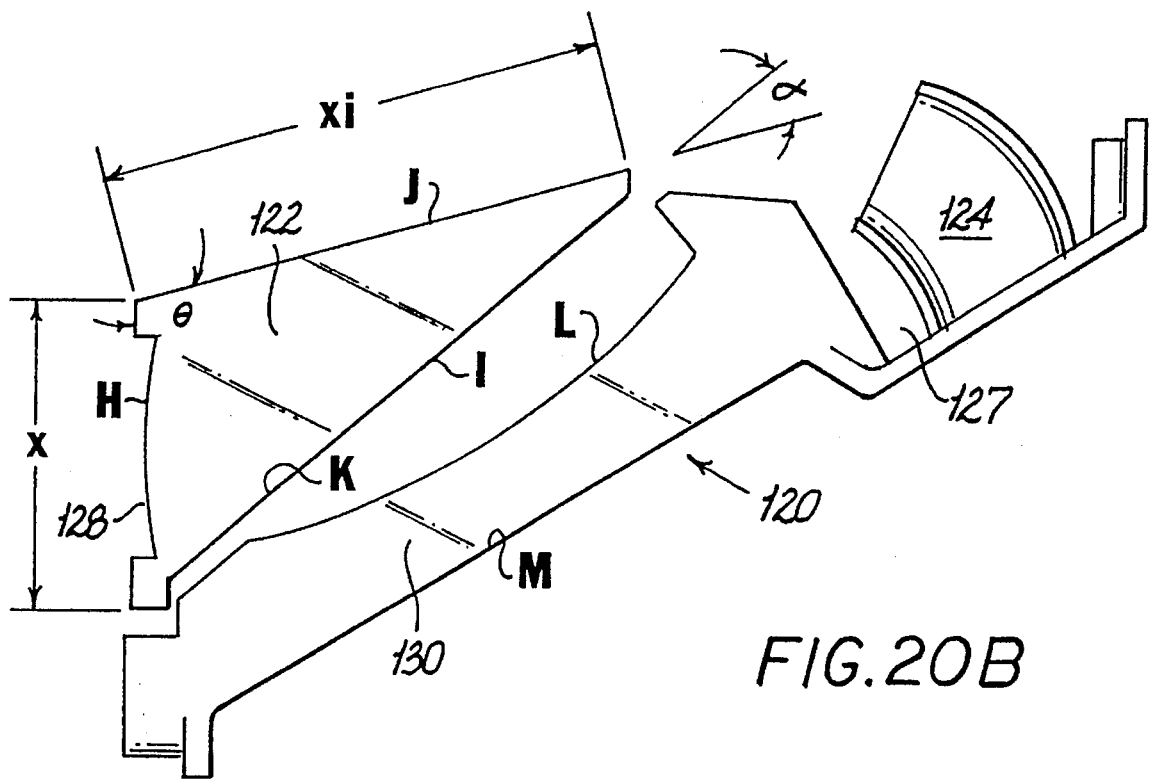
FIG. 20B is an enlarged side plan view showing the one-piece prism mount structure and the 60° prism.
Figure 21:
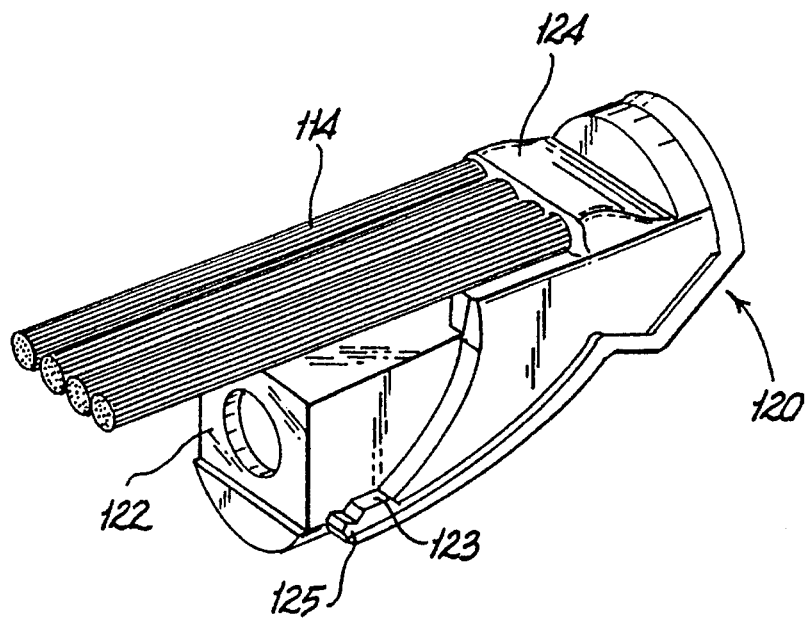
FIG. 21 is a perspective view of the prism mount of FIG. 18.

As best shown in FIG. 20B, the remaining optical components of prism mount 120 include convex lens surface 128 which is formed on the proximal surface of prism 122 and lens 130 molded into the mount. Lenses 128, 130 function in a similar manner to their corresponding lens components of the embodiment of FIGS. 1–4. Advantageously, prism mount 120 may be integrally molded of plastic or glass to include lens 130 and light guide 124 obviating the need for separate formation and mounting of these components. Further, as previously mentioned, the prism mount system advantageously includes wing portions 123 on the prism and flanges 125 on the mount for engaging and retaining prism 122, thereby facilitating assembly of prism to the mount in snap-fit relation. Thus, where prism mount 120 has integrally formed therein the concave lens 130, the device may be assembled by simple snap-fitting prism 122 onto mount 120, fitting mount 120 to sheath 112 with fibers 114 abutting total integral reflection light guide 124, and mounting the tip to the sheath. Prism mount 120 can engage sheath 112 by friction or other fit with or without adhesives or sealants, as required.

Referring to FIG. 20B, the geometrical characteristics of the optical components mounted in prism mount 120 are defined by lens surfaces H–N. The on-axis geometrical and optical parameters of the optical components are recorded in Table 3 below. Table 3 is as follows:

TABLE 3

| Surface | Radius | Thickness | Medium | Index |
| --- | --- | --- | --- | --- |
| H | 0.4671 | N/A | Polystyrene | 1.59 |
| I | Plano | N/A | Polystyrene | 1.59 |
| J | Plano | N/A | Polystyrene | 1.59 |
| K | Plano | 0.0793 | Air | 1.00 |
| L | 0.4904 | 0.0440 | Polystyrene | 1.59 |
| M | Plano | N/A | | |

FIG. 20B also illustrates the specific dimensions and angles of the optical components of prism mount 120. Table 4 outlines these dimensions in detail. Table 4 is as follows:

TABLE 4

| Surface or Angle | Dimension | Angle |
| --- | --- | --- |
| x | 0.2145 | N/A |
| xi | 0.3516 | N/A |
| θ | N/A | 99.5° |
| α | N/A | 28.5 |

Figure 22:
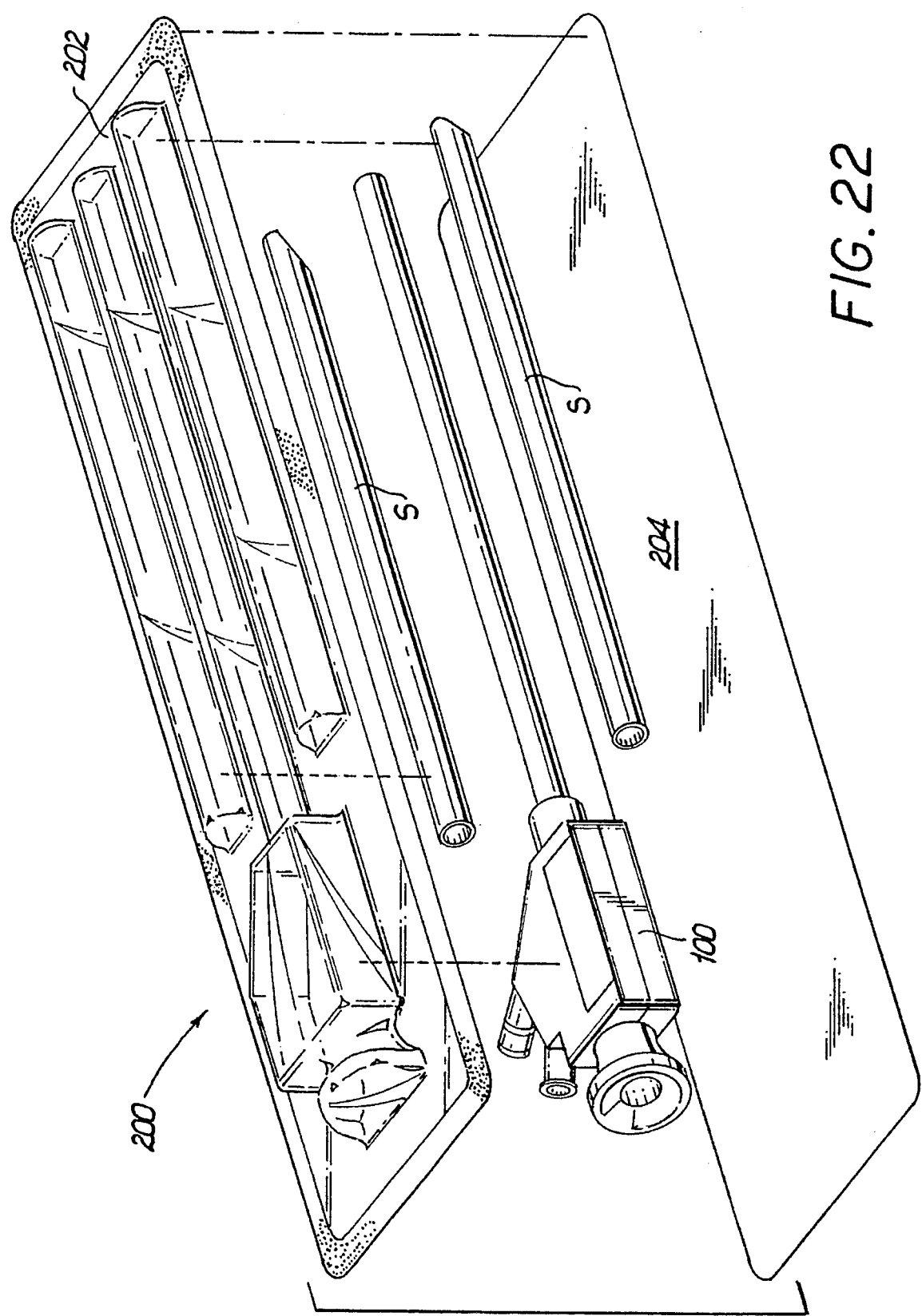
FIG. 22 is an exploded perspective view of a kit incorporating two endoscope sheaths of the present invention and packaged with an endoscope in a molded-type blister pack.

Referring now to FIG. 22, there is illustrated a kit 201 incorporating the previously described endoscope sheaths of the present invention. The kit 201 may include an endoscope 1000 and one or more of the endoscopic sheaths S each having a different angle of view. For example, sheaths with a 30° prism and/or a 60° prism can be packaged with an endoscope in a single kit so the user can select (and interchange) the sheath and place it over the endoscope prior to insertion into the body to achieve the desired angle of view in the surgical procedure. It is also envisioned that a 0° sheath could be included to protect the endoscope and maintain the cleanliness of the scope during non-oblique imaging. Thereafter, when a change of the angle of view is required to perform the surgery, a sheath incorporating a 30° or a 60° prism may be interchanged with the 0° sheath. A further advantage of a 0° sheath is that an improved illumination system having a higher transmission efficiency may be used in place of or to supplement the illumination system of the endoscope. Yet a further advantage is that an endoscope not having a fluid and/or gas conduit for cleaning the distal-most imaging lens and/or clearing the region in front of the distal-most lens can be provided with such a conduit by using a sheath having such a conduit. The package used may include a molded plastic cover or lid 202 and a base 204 which is secured to the lid along respective peripheral portions thereof. Alternatively, it is contemplated that a kit may be provided containing a plurality of endoscope sheaths without an endoscope. Such a kit may be useful, for example, with reusable endoscopes.

Figure 23:
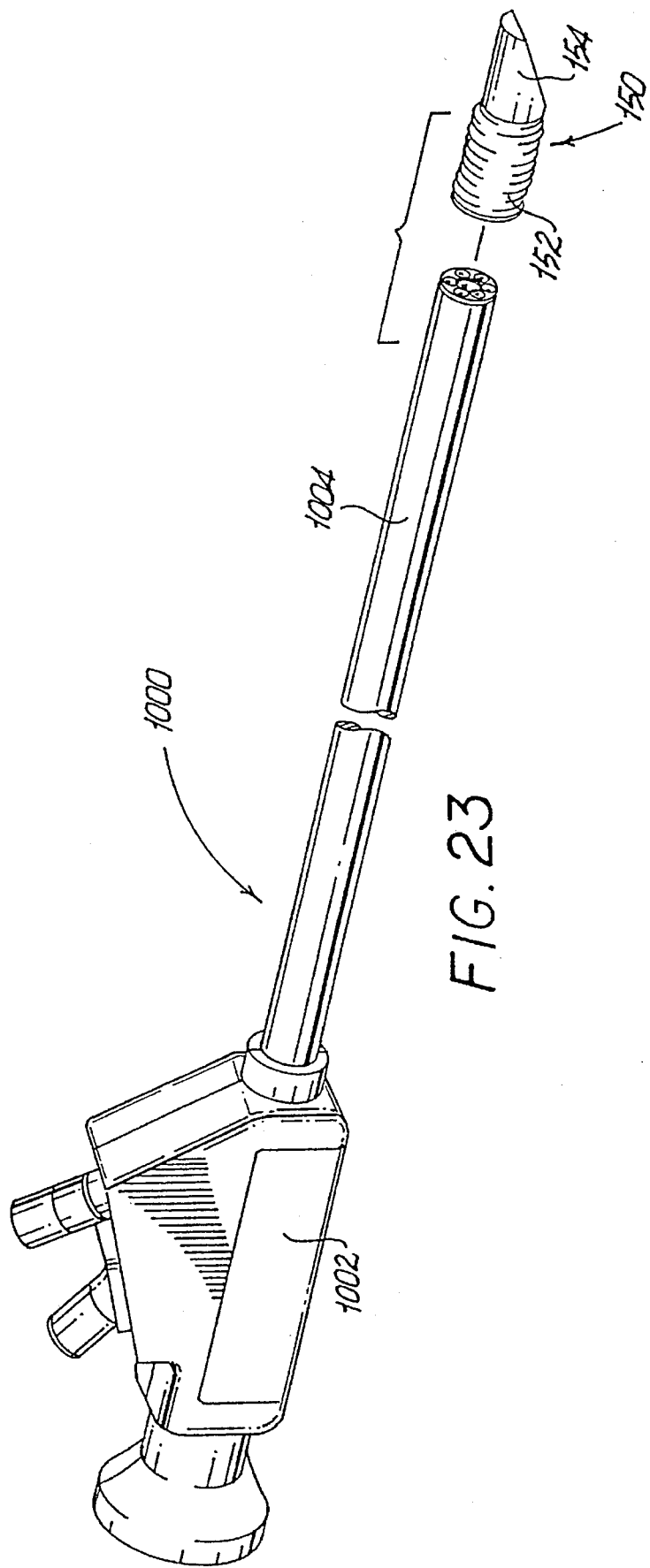
FIG. 23 is a perspective view of another alternative embodiment of the endoscope sheath of FIG. 1 including a flexible sheath portion with a distal tip connected thereto for housing a prism.
Figure 24:
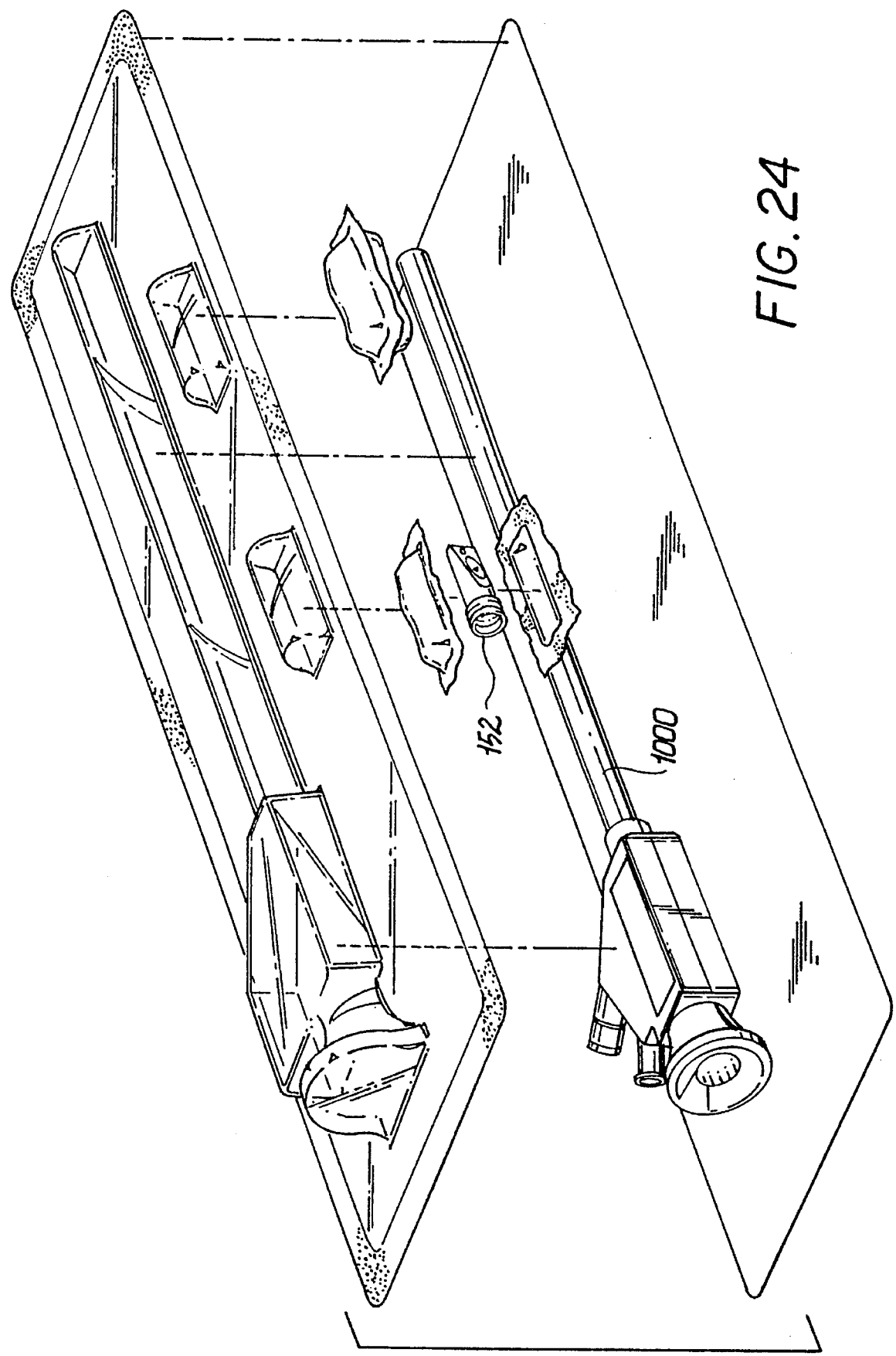
FIG. 24 is an exploded perspective view of a kit incorporating the endoscope sheath of FIG. 23 and packaged with an endoscope in a molded type blister pack.

Referring now to FIG. 23, there is illustrated another alternative embodiment of the endoscope sheath of the present invention. Endoscope sheath 150 includes elastic sheath member 152 which is fabricated from a flexible material such as latex rubber and is attached to prism mount 154 in any known manner such as by welding, adhesives or the like. The elastic sheath 152 may be pulled onto endoscopic portion 1004 and extend proximally to enclose substantially all of the elongated endoscopic portion of the endoscope. Elastic sheath 152 is preferably dimensioned to form a snug fit about the endoscopic portion 1002. Prism mount 154 includes a prism to change the angle of view as previously described. This embodiment of endoscopic sheath may have particular application with flexible endoscopes. FIG. 24 illustrates the endoscope sheath 150 of FIG. 23 packaged along with a conventional endoscope 1000 as part of a kit having a 30° endoscope sheath and 60° endoscope sheath.

While the invention has been particularly shown and described with reference to the preferred embodiments, it will be understood by those skilled in the art that various modifications and changes in form and detail may be made without departing from the scope and spirit of the invention. For example, it is conceivable that other prisms such as 45° prism or right angle prism may be readily employed. Additionally, plural prism systems, and rotatable prisms which change the angle of view from forward to side viewing, e.g., roof prisms can also be utilized. Such rotatable prisms may be controlled proximally by the user. Accordingly, modifications such as those suggested above, but not limited thereto, are to be considered within the scope of the invention.

What is claimed is:

1. An endoscopic instrumentation kit comprising:
    an endoscope having imaging optics with a defined angle of view;
    at least one endoscopic sheath, said one sheath comprising a distal portion configured to be positioned adjacent a distalmost portion of said endoscope imaging optics, said distal portion including means for changing the angle of view of said imaging optics to define an inclined angle of view inclined relative to a longitudinal axis of said one sheath, and a proximal portion attached to said distal portion, said proximal portion configured and dimensioned to substantially enclose the endoscopic portion of said endoscope, said one sheath further including an integral illumination system for transferring illuminating light, the illumination system having structure to direct light in general alignment with the inclined angle of view; and
    a package including a top cover and a bottom cover, said top and bottom covers forming a package containing said endoscope and said at least one endoscopic sheath.

2. The endoscopic instrumentation kit of claim 1 comprising a plurality of endoscopic sheaths including at least an endoscopic sheath for changing the endoscope field of view by about 30° and an endoscopic sheath for changing the endoscope field of view by about 60°.

3. The endoscopic instrumentation kit of claim 1 wherein the proximal portions of said one endoscopic sheath is made of a rigid material.

4. The endoscopic instrumentation kit of claim 1 wherein at least one of said top and bottom covers is provided with form fitting cavities configured substantially to the shape of at least one of said endoscope and said one endoscopic sheath.

5. The endoscopic instrumentation kit of claim 1 wherein said illumination system of said one endoscopic sheath includes at least one optical fiber extending at least the length of said endoscopic sheath.

6. The endoscopic instrumentation kit of claim 5 wherein said endoscopic sheath includes a longitudinal channel in a side wall thereof, said longitudinal channel accommodating at least a portion of said at least one optical fiber of said illumination system.

7. The endoscopic instrumentation kit of claim 5 wherein said illumination system includes a prism in optical alignment with said one optical fiber, said prism directing light emitted by said one optical fiber into the inclined angle of view.

8. The endoscopic instrumentation kit of claim 1 wherein said means for changing the angle of view of said imaging optics includes a prism.

9. The endoscopic instrumentation kit of claim 8 wherein said distal portion of said at least one endoscopic sheath includes a prism mount, said prism mount having said prism supported therein.

10. The endoscopic instrumentation kit of claim 9 wherein said prism mount includes two opposed openings formed in a peripheral wall thereof, said prism being supported by portions of said prism mount defining said two opposed openings.

11. The endoscopic instrumentation kit of claim 10 wherein said prism mount has a channel dimensioned to accommodate a distal end portion of said at least one optical fiber of said illumination system, said channel being angularly oriented relative to a longitudinal axis defined by said endoscopic sheath such that said distal end portion of said at least one optical fiber is angularly oriented relative to said longitudinal axis to emit light into an angle of view defined by said means for changing the angle of view of said imaging means.

12. An endoscopic instrumentation kit comprising:
   an endoscope having imaging optics with a defined angle of view;
   at least one endoscopic sheath, said sheath comprising a distal portion configured to be positioned adjacent a distalmost portion of an endoscope imaging optics, said distal portion including means for changing the angle of view of said imaging optics and a proximal portion attached to said distal portion, said proximal portion configured and dimensioned to substantially enclose the endoscopic portion of said endoscope, said one endoscopic sheath being flexible along the length thereof; and
   a package including a top cover and a bottom cover, said top and bottom covers forming a package containing said endoscope and said one endoscopic sheath.

13. An endoscopic instrumentation kit comprising:
   a plurality of endoscopic sheaths, each said sheath configured to be positionable on an endoscope having imaging optics with a defined angle of view, each said sheath having a distal portion configured to be positioned adjacent a distalmost portion of an endoscope imaging optics, said distal portion including means for changing the angle of view of the endoscope imaging optics to define an inclined angle of view inclined relative to a longitudinal axis of sheath, and a proximal portion attached to said distal portion, said proximal portion configured and dimensioned to substantially enclose an endoscopic portion of said endoscope, each said sheath further including an illumination system for transferring illuminating light from an external light source to at least said distal portion, said illumination system having means to direct light in general alignment with the inclined angle of view; and
   a package including first and second portions, said first and second portions together forming a package containing said endoscopic sheaths.

14. The endoscopic instrumentation kit of claim 13 wherein said plurality of endoscopic sheaths include at least an endoscopic sheath for changing the endoscope field of view by about 30° and an endoscopic sheath for changing the endoscope field of view by about 60°.

15. The endoscopic instrumentation kit of claim 13 wherein the proximal portions of said endoscopic sheaths are made of a rigid material.

16. The endoscopic instrumentation kit of claim 13 wherein the proximal portions of said endoscopic sheaths are made of a flexible material.

17. The endoscopic instrumentation kit of claim 13 wherein said plurality of endoscopic sheaths include at least an endoscopic sheath for changing the angle of view by about 30° and an endoscopic sheath for changing angle of view by about 0°.

18. The endoscopic instrumentation kit of claim 13 wherein said illumination system includes at least one optical fiber extending at least partially along the length of each said endoscopic sheath.

19. The endoscopic instrumentation kit of claim 18 wherein a distal end portion of said one optical fiber of said illumination system is angularly oriented relative to the longitudinal axis to direct light into the inclined angle of view.

20. The endoscopic instrumentation kit of claim 18 wherein said means to direct light includes a prism disposed in general alignment with said one optical fiber, said prism directing light emitted by said one optical fiber in general alignment with the inclined angle of view.

21. An endoscopic instrumentation kit which comprises:
   an endoscope having imaging optics with a defined angle of view;
   at least one endoscopic sheath including an elongated tubular member having proximal and distal end portions and defining a longitudinal bore configured and dimensioned for enclosing an endoscopic portion of the endoscope, the endoscopic sheath further including an illumination system for transferring illuminating light from an external light source to at least the distal end portion of the elongated member, the illumination system configured and dimensioned to direct light in general alignment with an inclined angle of view angularly offset relative to a longitudinal axis of said tubular member; and
   a package including a top cover and a bottom cover, the top and bottom covers forming a package containing said endoscope and said at least one endoscopic sheath.

* * * * *